(12) United States Patent
Sadeghi

(10) Patent No.: US 10,456,419 B2
(45) Date of Patent: Oct. 29, 2019

(54) METHOD FOR TREATING MIGRAINE HEADACHES

(71) Applicant: Payman Sadeghi, Miami, FL (US)

(72) Inventor: Payman Sadeghi, Miami, FL (US)

(*) Notice: Subject to any disclaimer, the term of this patent is extended or adjusted under 35 U.S.C. 154(b) by 0 days.

(21) Appl. No.: 15/907,074

(22) Filed: Feb. 27, 2018

(65) Prior Publication Data

US 2018/0243339 A1    Aug. 30, 2018

Related U.S. Application Data

(60) Provisional application No. 62/600,726, filed on Feb. 27, 2017.

(51) Int. Cl.
| | | |
|---|---|---|
| *A61K 35/16* | (2015.01) | |
| *A61B 5/00* | (2006.01) | |
| *A61B 17/34* | (2006.01) | |
| *A61K 35/28* | (2015.01) | |
| *A61K 9/00* | (2006.01) | |
| *C12N 5/0775* | (2010.01) | |

(52) U.S. Cl.
CPC ............ *A61K 35/16* (2013.01); *A61B 5/4076* (2013.01); *A61B 17/3421* (2013.01); *A61B 17/3472* (2013.01); *A61K 35/28* (2013.01); *A61K 9/0019* (2013.01); *C12N 5/0667* (2013.01)

(58) Field of Classification Search
None
See application file for complete search history.

(56) References Cited

U.S. PATENT DOCUMENTS

| | | |
|---|---|---|
| 5,443,850 A | 8/1995 | Thys-Jacobs |
| 5,676,691 A | 10/1997 | Friedman |
| 5,977,145 A | 11/1999 | Silberstein et al. |
| 6,432,986 B2 | 8/2002 | Levin |
| 6,735,475 B1 | 5/2004 | Whitehurst et al. |
| 7,704,511 B2 | 4/2010 | Turkel et al. |
| 8,198,240 B2 | 6/2012 | Yeomans et al. |
| 8,202,838 B2 | 6/2012 | Yeomans et al. |
| 8,252,745 B2 | 8/2012 | Yeomans et al. |
| 8,501,691 B2 | 8/2013 | Yeomans et al. |
| 8,562,973 B2 | 10/2013 | Edinger et al. |
| 8,691,769 B2 | 4/2014 | Borodic et al. |
| 8,828,376 B2 | 9/2014 | Zeitlin et al. |
| 8,889,151 B2 | 11/2014 | Turkel et al. |
| 9,078,893 B2 | 7/2015 | Turkel et al. |
| 2012/0101479 A1 | 4/2012 | Paspaliaris et al. |
| 2012/0164113 A1 | 6/2012 | Victor |
| 2013/0189234 A1 | 7/2013 | Victor |
| 2014/0017209 A1 | 1/2014 | Aberman et al. |
| 2015/0159151 A1 | 6/2015 | Bright et al. |
| 2015/0174172 A1 | 6/2015 | Bright et al. |
| 2016/0030488 A1 | 2/2016 | Fischkoff et al. |

FOREIGN PATENT DOCUMENTS

| | | |
|---|---|---|
| CA | 2877022 A1 | 1/2014 |
| CN | 104704111 A | 6/2015 |
| CN | 104902909 A | 9/2015 |
| EP | 2863927 A1 | 4/2015 |
| JP | 2015521630 A | 7/2015 |
| KR | 20150091037 A | 8/2015 |
| WO | 2012127320 A1 | 9/2012 |
| WO | 2014000029 A1 | 1/2014 |
| WO | 2014000031 A1 | 1/2014 |

OTHER PUBLICATIONS

Bright et al., Migraine and tension-type headache treated with stromal vascular fraction: a case series, 2014, Journal of Medical Case Reports 2014, 8:237 http://www.jmedicalcasereports.com/content/8/1/237, 5 pages (Year: 2014).*

Mauskop et al., Stem Cells in the Treatment of Refractory Chronic Migraines, 2017, Case Rep Neurol 9:149-155 (Year: 2017).*

* cited by examiner

*Primary Examiner* — John D Ulm
(74) *Attorney, Agent, or Firm* — Dickinson Wright PLLC

(57) ABSTRACT

A method for preventing and treating a headache in a patient is disclosed. The method includes locating one or more ligaments or muscle insertions that are associated with a cervical spine and a skull of the patient. The method further includes injecting into the determined one or more ligaments or muscle insertions an injectable regenerative solution that is derived from the patient to repair the one or more ligaments or muscle insertions. The method may further include determining a locus of the headache in the patient, determining one or more nerves associated with the locus of the headache, determining a set of the one or more ligaments or muscle insertions that are associated with the one or more nerves, and injecting the injectable regenerative solution into the determined set of the one or more ligaments or muscle insertions.

20 Claims, 6 Drawing Sheets

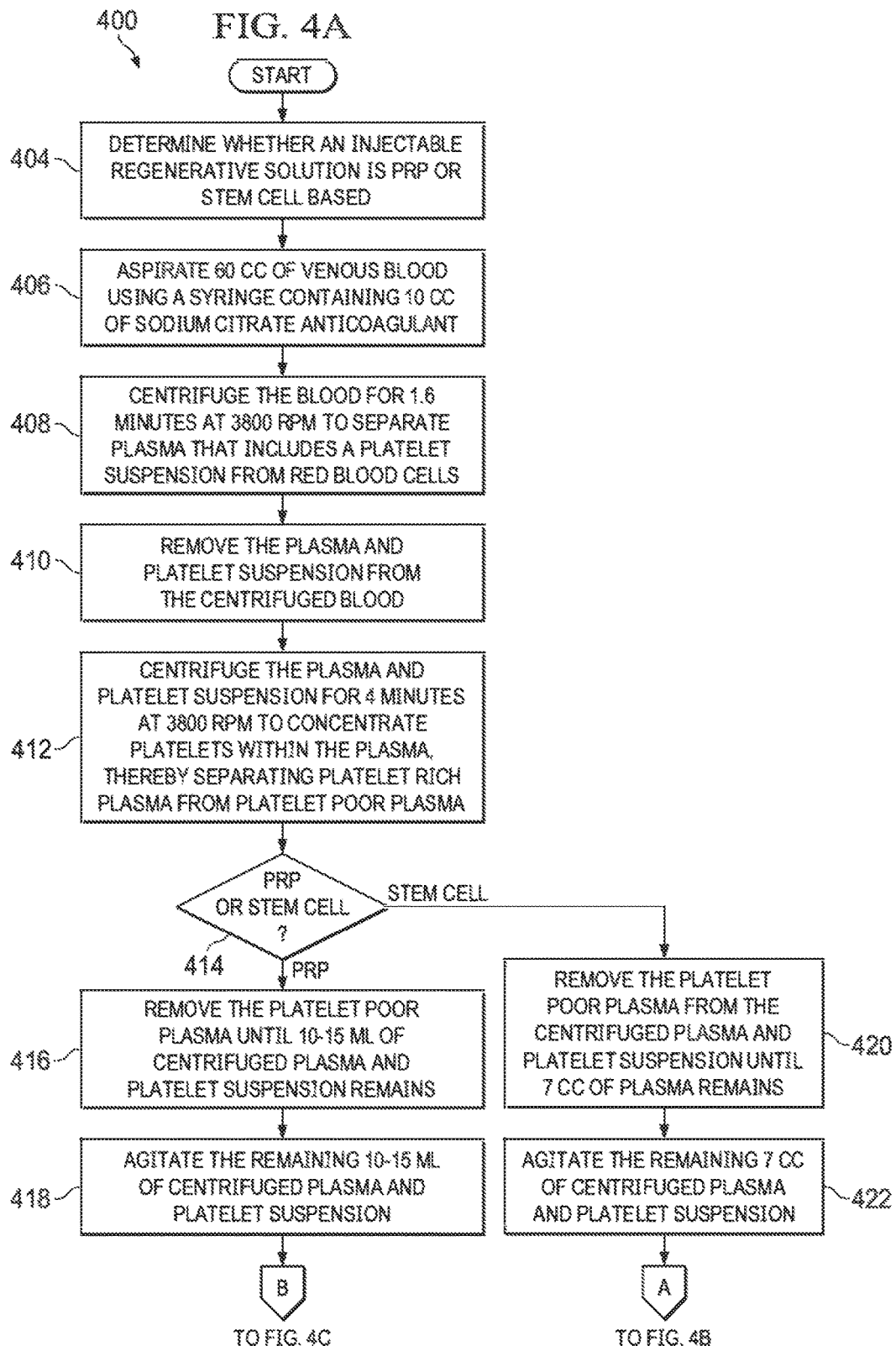

METHOD FOR TREATING MIGRAINE HEADACHES

CROSS-REFERENCE TO RELATED APPLICATION(S) AND CLAIM OF PRIORITY

This application claims priority under 35 U.S.C. § 119(e) to U.S. Provisional Patent Application No. 62/600,726 filed on Feb. 27, 2017. The above-identified provisional patent application is hereby incorporated by reference in its entirety.

TECHNICAL FIELD

This disclosure relates generally to regenerative tissue therapy. Specifically, this disclosure relates to a method for treating migraine headaches by applying regenerative injections to ligaments and muscles supporting the cervical spine of a patient.

BACKGROUND

Migraine headaches can be a debilitating problem for people who suffer them. In some estimates up to 15% of people globally are affected by migraines. Migraine headaches are typically recurrent, often start during puberty, and get worse during middle age. The symptoms may be quite severe and may include nausea, vomiting, and sensitivity to outside influences such as light, sound, or even smell. Unfortunately, migraines can be long lasting—sometimes up to three days or more.

SUMMARY

Embodiments of the present disclosure provide a method for treating migraine headaches by applying regenerative injections to ligaments and muscles supporting the cervical spine of a patient.

In one embodiment, a method for preventing and treating a headache in a patient is disclosed. The method includes locating one or more ligaments or muscle insertions that are associated with a cervical spine and a skull of the patient. The method further includes injecting into the determined one or more ligaments or muscle insertions an injectable regenerative solution that is derived from the patient to repair the one or more ligaments or muscle insertions. The method may further include determining a locus of the headache in the patient, determining one or more nerves associated with the locus of the headache, determining a set of the one or more ligaments or muscle insertions that are associated with the one or more nerves, and injecting the injectable regenerative solution into the determined set of the one or more ligaments or muscle insertions.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The terms "include" and "comprise," as well as derivatives thereof, mean inclusion without limitation. The term "or" is inclusive, meaning and/or. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIGS. 4A-4C illustrate a flow diagram of an example method for treatment of migraines or other headaches.

DETAILED DESCRIPTION

Figure 1:
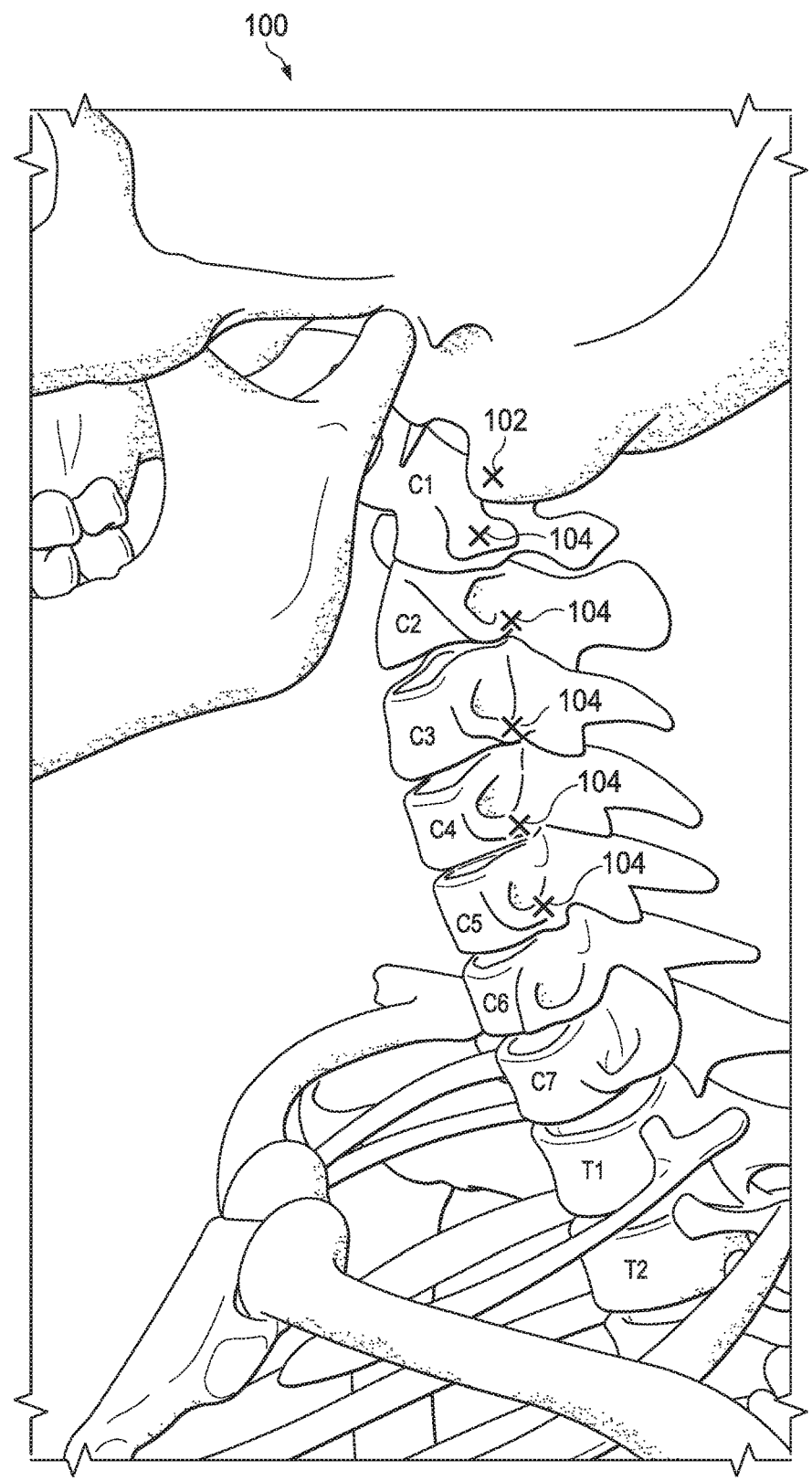
FIG. 1 illustrates a portion of an example injection scheme from a lateral view of the patient, showing injection sites at the mastoid process and the transverse process of the C1 to C5 vertebrae.

FIGS. 1 through 4C, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

The underlying mechanisms of migraine headaches (or migraines) are not fully known, but most current theories for the cause of migraines are central (i.e., thought to involve the nerves and blood vessels of the brain). Embodiments of the present disclosure contemplate that migraines and headaches are a peripheral nerve disorder (i.e., involving nerves and blood vessels outside of the brain) and not a central one.

Embodiments of the present disclosure contemplate that the most common cause of migraines and most other headache syndromes such as cluster, tension, and primary exertional headaches is cervical spine problems. The most prominent problem in the cervical spine region stems from laxity and injury to the ligaments, tendons, and fascia of the region. Such laxity and injury could be the result of an injury (such as a motor vehicle accident), a fall, or head trauma (such as concussion) in which whiplash injury to the neck is an almost ubiquitous comorbidity. Ligament laxity and injury could also result from repetitive injury, such as bad posture, or a sedentary life style, such as a lifestyle involve heavy use of computers or other electronics.

Regardless of the cause, ligament injury and laxity causes instability of the spinal column that in turn causes irritation of the nerves and inflammation of the facet joints (the uncovertebral joints). Without support from the ligaments, muscles surrounding the facet joints will go into spasm in an attempt to guard and provide some stability to the spine. Such muscle spasm causes the pressure, squeezing, and vice grip type headache. The nerve root irritation causes many different types of pain sensations such as burning, tingling, shocking, stabbing, lightning, and throbbing.

The pain caused by the muscle spasm and nerve irritation causes a cascade of symptoms. As the pain gets more intense, there will be central sensitization of the nervous system of the patient, which lowers the patient's pain threshold. At this time, the patient's brain senses danger around it because of the head pain, and this can cause photophobia, phonophobia, nausea, vomiting, and other symptoms that accompany migraines. Additionally, due to the above-described laxity of the ligaments, the cervical autonomic chain of ganglions (which is anterior to the facet joints and transverse process of the upper cervical vertebrae) may get irritated with every head and neck motion. This irritation of the cervical autonomic chain can cause other autonomic or dysautonomic symptoms such as teary eye, red eye, nasal congestion, nausea, vomiting, dizziness, and so forth. This is known as Barre-Lieou Syndrome, and was described by Dr. Barre in France and Dr. Lieou in China during World War I.

If the above-described damage to the ligaments is repaired, stability is restored to the spine and the various connected parts of the skull, including the lateral and anterior parts of the skull. When this stability is restored, the symptoms, including headaches and migraines, show improvement. However, ligaments, tendons, and cartilages do not repair themselves because there is not enough blood flow to them to facilitate self-repair.

Accordingly, the present disclosure contemplates the use of regenerative treatments to repair damaged ligaments, tendons, and cartilages. More specifically, this disclosure relates to the repair of damaged ligaments, tendons, and cartilages that support the cervical spine region using a regenerative solution of platelet rich plasma (PRP) or stem cells. The methods of this disclosure use autologous bone marrow or adipose derived stem cells, but it is understood that stem cells derived from other appropriate locations may be used. In the methods of this disclosure, stem cells are mixed with PRP to activate the stem cells.

The PRP or stem cell regenerative solution is then injected into a problem area. The problem area can include, but is not limited to, the superior and inferior occipital ridges of the skull, the mastoid process of the skull, the transverse processes of the C1 to C6 vertebrae, and the spinous processes, laminae, and facet joints of the C2 to C7 vertebrae. Injection of the $1^{st}$ and $2^{nd}$ ribs bilaterally (at the scalene muscle insertions), the medial manubrium bilaterally, or the clavicle (at the sternocleidomastoid or trapezius muscle insertions) may be necessary in some patients.

A follow up checkup may be performed on the patient 4-5 weeks after these injections to evaluate progress and remaining symptoms of migraine. Depending on the patient's progress and symptoms, the same procedure may be repeated, the scapulas may be treated, the shoulders may be treated, or all of the above.

After injection of the regenerative solution to the ligaments, tendons, and cartilages, stability is restored to the cervical spine and skull. As a result, nerves and muscles are no longer irritated by normal movements and migraine symptoms will be resolved. In some cases, symptoms caused by various non-mechanical migraine triggers such as food, wine, odors, weather changes, etc., are resolved as well.

The choice between use of PRP or stem cells in the regenerative solution depends on the patient. Stem cells are more effective than a pure PRP solution, but the stem cell treatment is more complicated and costly due to the harvesting of the stem cells from the patient, as will be further described below.

Referring now to FIG. 1, there is illustrated a portion of an example injection scheme from a lateral view 100 of the patient, showing injection sites at the mastoid process and the transverse process of the C1 to C5 vertebrae. While FIG. 1 illustrates injection sites on the skeletal structure of the patient, the injections are to be applied to the ligaments, tendons, or cartilages that attach to the indicated injection sites.

Each "x" in FIG. 1 indicates an injection site. An injection site 102 is located at the mastoid process of the skull of the patient. An injection site 104 is also located at each transverse process of the C1 to C5 vertebrae. Although FIG. 1 illustrates only one side of the patient, injections should be performed bilaterally (i.e., at matching sites on the opposite side of the patient).

Figure 2:
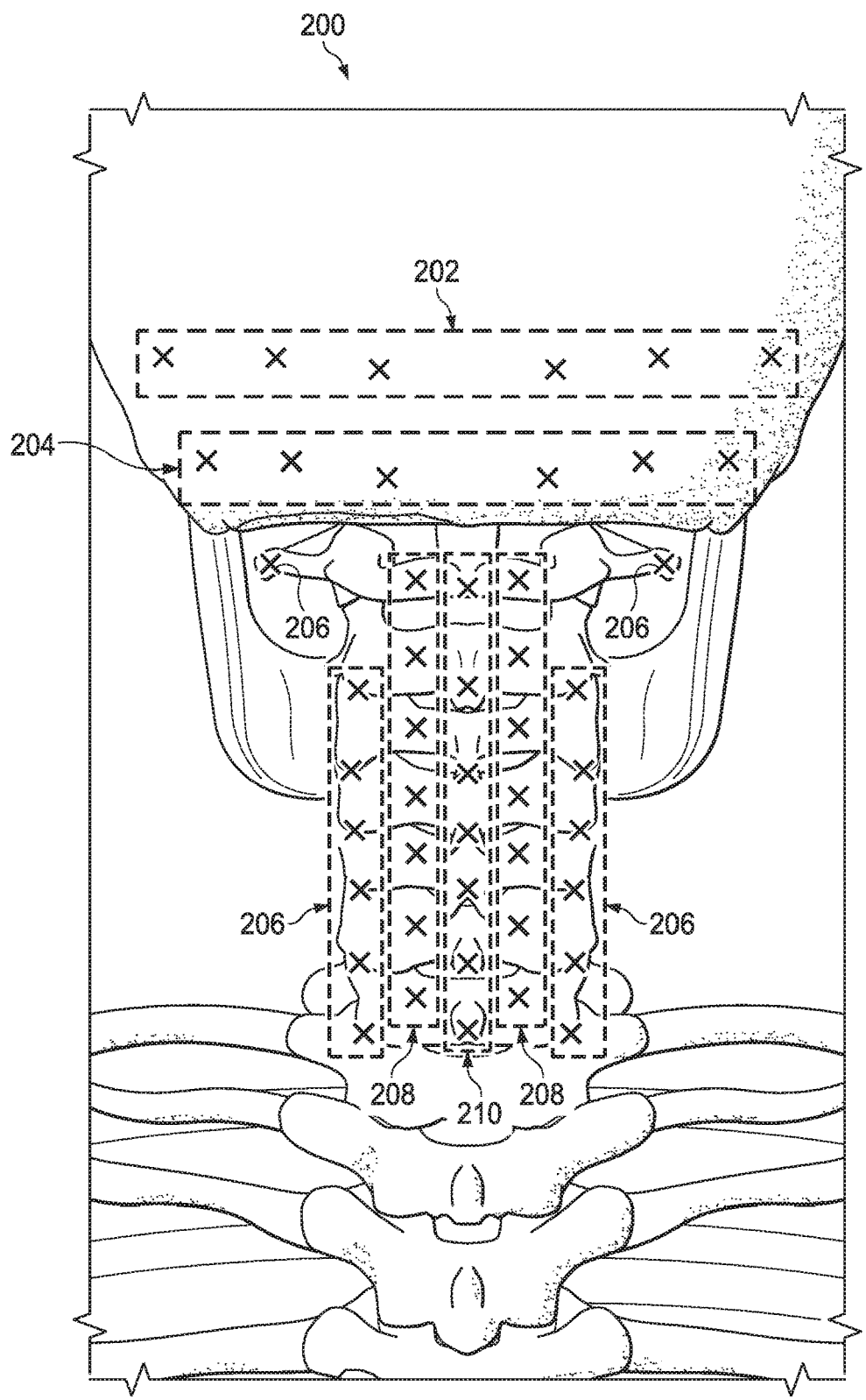
FIG. 2 illustrates another portion of the example injection scheme from a posterior view of the patient, showing injection sites at the superior and inferior occipital ridges of the skull, at the spinous processes of the C2 to C7 vertebrae, and bilaterally at the laminae and facet joints of the C2 to C7 vertebrae.

Referring now to FIG. 2, there is illustrated another portion of the example injection scheme from a posterior view 200 of the patient, showing injection sites at the superior and inferior occipital ridges of the skull, at the spinous processes of the C2 to C7 vertebrae, and bilaterally at the laminae and facet joints of the C2 to C7 vertebrae. While FIG. 2 illustrates injection sites on the skeletal structure of the patient, the injections are to be applied to the ligaments, tendons, or cartilages that attach to the indicated injection sites.

As above, each "x" in FIG. 2 indicates an injection site. Injection sites 202 (illustrated as enclosed by a box for clarity) are located along the superior occipital ridge of the skull of the patient. Injection sites 204 (illustrated as enclosed by a box for clarity) are located along the inferior occipital ridge of the skull of the patient. Injection sites 206 are located bilaterally at the facet joints of each of the C1 to C7 vertebrae. The injection sites 206 at the C2-C7 vertebrae are illustrated as enclosed by a box and the injection sites 206 at the C1 vertebra are indicated separately for clarity. Injection sites 208 (illustrated as enclosed by a box for clarity) are located bilaterally at the laminae of each of the C1-C7 vertebrae. Injection sites 210 (illustrated as enclosed by a box for clarity) are located at the spinous processes of each of the C1-C7 vertebrae.

Figure 3:
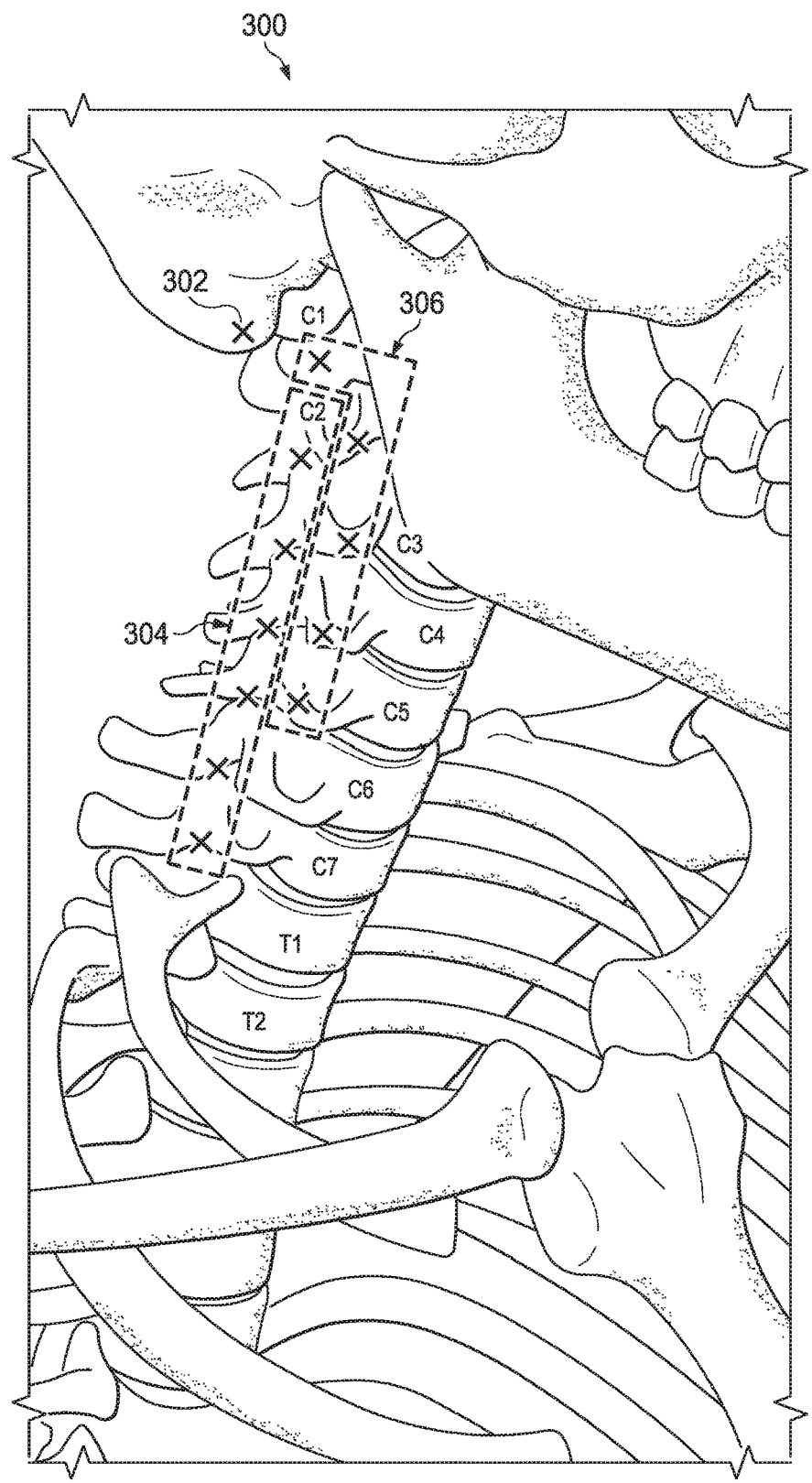
FIG. 3 illustrates another portion of the example injection scheme from an anterolateral view of the patient, showing injection sites at the mastoid process of the skull, the transverse processes of the C1 to C5 vertebrae, and the facet joints of the C2 to C7 vertebrae.

Referring now FIG. 3, there is illustrated another portion of the example injection scheme from an anterolateral view 300 of the patient, showing injection sites at the mastoid process of the skull, the transverse processes of the C1 to C5 vertebrae, and the facet joints of the C2 to C7 vertebrae. While FIG. 3 illustrates injection sites on the skeletal structure of the patient, the injections are to be applied to the ligaments, tendons, or cartilages that attach to the indicated injection sites.

As above, each "x" in FIG. 3 indicates an injection site. Injection site 302 is located at the mastoid process of the skull of the patient. Injection sites 304 (illustrated as enclosed by a box for clarity) are located at the facet joints of each of the C2 to C7 vertebrae. Injection sites 306 (illustrated as enclosed by a box for clarity) are located at the transverse processes of each of the C1 to C5 vertebrae. Although FIG. 3 illustrates only one side of the patient, injections should be performed bilaterally (i.e., at matching sites on the opposite side of the patient).

As discussed above, either a PRP or a stem cell solution including PRP is injected at the above injection sites as a regenerative solution. PRP is a component of a patient's blood, and can be prepared, in some embodiments, as follows. First, 10 cc of sodium citrate anticoagulant is drawn (or aspirated) into a 60 cc syringe. Then, using an 18 or 19-gauge butterfly needle, 50 cc of venous blood is drawn into the same syringe. A large-bore needle is recommended in order to prevent damage to the platelets in the blood, however, if it is difficult to draw the patient's blood with an 18 or 19-gauge needle, a smaller bore needle may be used.

The 60 cc of anticoagulated blood in the syringe is transferred into a centrifuge tube and is centrifuged for 1.5 minutes at 3800 RPM. After this initial centrifugation, plasma and platelet suspension is separated from the red blood cells. The plasma and platelet suspension is then aspirated into a 60 cc syringe and transferred into a second centrifugation tube. The plasma and platelet suspension is then centrifuged for 5 minutes at 3800 RPM. This second centrifugation step separates platelet concentrates from the plasma in the form of a buffy coat at the bottom of the tube, leaving a platelet poor plasma.

Some of the platelet poor plasma is then aspirated out of the tube. When preparing pure PRP for use as the regenerative solution, 10-15 mL of the plasma is left in the tube. The tube is then agitated with a swirling movement to re-suspend the platelet buffy coat into the plasma. The final product is pure PRP. When preparing PRP to be mixed with stem cells as an activator for the stem cells, a smaller amount (e.g., 7 cc) of plasma is left in the tube before agitation to re-suspend the platelet buffy coat into the plasma. This creates a more concentrated PRP.

If using only PRP as the regenerative solution, the PRP can be mixed with 5 cc of ropivacaine 0.2% before injection for the patient's comfort. Ropivacaine acts as a local anesthetic and does not have any other therapeutic value. Ropivacaine is preferred over other local anesthetics, such as lidocaine, because it is less toxic to platelets. The PRP and local anesthetic solution can be drawn into a 5 cc syringe for each injection site.

When preparing a regenerative solution using stem cells, either adipocyte (i.e., fat) or bone marrow stem cells are used. In one embodiment, a regenerative solution of adipocyte stem cells is prepared as follows.

First, the right or left abdominal lower quadrant of the patient is localized. Through palpation and other physical exam methods any organomegaly should be evaluated. If all is normal with the area, it is thoroughly cleaned with chlorhexidine and a sterile draping is applied. A rectangular area about 15 cm long by 7-8 cm wide is drawn. Dermal and subcutaneous local anesthesia is applied at the tips of the rectangle (e.g., lidocaine 1% with epinephrine). Using a #11 scalpel a small stab wound is created at the anesthetized site.

10 cc of lidocaine 1% with epinephrine and 50 cc of normal saline are drawn into each of two 60 cc syringes. A first syringe of the two 60 cc syringes is then attached to a tulip infiltrating cannula. The tip of the cannula is slowly inserted into the small stab wound and the subcutaneous adipose tissue. The cannula is slowly advanced within the previously drawn rectangle while slowly pushing the anesthetic saline solution into the area. Once the first syringe is emptied the procedure is repeated with the second 60 cc syringe. The entire rectangular area that was drawn on patient's abdominal quadrant should be covered with the solution, ensuring proper anesthesia of the area to be worked on.

Once the anesthetic is properly applied, the subcutaneous fat of the patient is broken off through mechanical agitation using the same infiltrating cannula. Rapid, sturdy back and forth movement of the syringe and cannula in the area is the preferred method to loosen up the subcutaneous fat.

Next, a tulip harvester is attached to a 30 cc syringe, and about one fourth of the harvester is inserted into the previously created stab wound. Vacuum is created by pulling the plunger of the syringe back about 5-10 cc. A back-and-forth motion in different directions in the same rectangular area is performed while keeping backwards pressure on the plunger. This causes more fat globules to be broken off from the subcutaneous tissue and to be collected into the syringe. Once the 5-10 cc is filled, the plunger is pulled back to 15-20 cc and the same motion is repeated until there is about 30 cc total of fat in the syringe. The above process is repeated using another 30 cc syringe, collecting a total of about 60 cc of fat aspirate. An appropriate bandage is then applied to the extraction sites.

The 60 cc of fat aspirate from both syringes is mechanically agitated using two 60 cc syringes attached to a 3-way stopcock. The fat aspirate is pushed back and forth through the stopcock from one syringe into the other syringe several times in order to break down any large pieces of adipose tissue. The fat aspirate is then transferred into centrifugation tubes and centrifuged for 3.5 minutes at 1500 RPM. The solution is divided into 3 layers by the centrifugation. The first layer (tumescent fluid) is discarded. The second layer is a concentrated adipose tissue solution, and is aspirated into a 30 cc syringe. This solution is again mechanically agitated using 2 syringes attached together through an emulsifier. The solution is pushed back and forth between the 2 syringes through the emulsifier about 10-15 times. This further breaks down large portions of tissue in the concentrated adipose tissue.

To prepare the final regenerative solution, about 23 cc of the adipose tissue concentrate and 7 cc of the concentrated PRP (as prepared above) are mixed together. 5 cc of ropivacaine 0.2% is added to this solution as an anesthetic in order to provide more comfort for the patient during the injection. The resulting solution is the final adipocyte based regenerative solution and it is ready to be injected into appropriate sites. A 5 cc syringe of the regenerative solution is prepared for each injection site using the appropriate needle gauge and length for the patient's body habitus. A 23G 2 inch needle is usually an appropriate choice.

In one embodiment, a regenerative solution of bone marrow stem cells is prepared as follows. First, 15 cc of heparin 1000 U/mL is drawn into a 60 cc syringe. The syringe and the needle are withdrawn from the heparin vial and the plunger is pulled back to 60 cc mark. The syringe is moved around such that the heparin touches all surfaces of the empty syringe. This process helps to heparinize the surfaces of the syringe to prevent coagulation of bone marrow when it is collected. The plunger is then moved back to the 15 cc mark, right at the level of the heparin content.

A bone marrow aspiration needle (e.g., an 11-gauge 11 cm needle) is attached to the syringe. About 1-2 cc of heparin is pushed through the needle so that it covers the inside and spills over from the top. This process heparinizes the bone marrow aspiration needle to prevent coagulation of bone marrow when it is collected. The syringe, which now contains about 13-14 cc of heparin, is attached to a 270 micron filter and 3-4 cc of heparin is pushed into the filter from the entrance point and removed by another syringe at the exit point. At this point, 10 cc of heparin is left in the 60 cc syringe. All materials are then heparinized and ready to be used.

In at least one embodiment, the left or right posterior superior iliac spine (PSIS) of the patient is localized. A side of the patient is chosen based upon the patient and the doctor's comfort. The area is thoroughly cleaned with chlorhexidine to sterilize the area. The skin and the tissue overlaying the PSIS is anesthetized using lidocaine 1% with epinephrine. A needle of a syringe containing the anesthetic is inserted into the area and is advanced to the periosteum, and anesthesia is applied to periosteum as well. Using a #11 scalpel blade a small stab wound is created.

The bone marrow aspiration needle is then inserted into the stab wound and advanced towards the PSIS periosteum. When the tip of the needle is on the periosteum, the doctor starts applying a firm and constant, controlled, downward pressure with rotating movement to drive the needle into the bone while giving attention to the amount of resistance felt. When the resistance drops, the needle is most likely in the bone marrow cavity.

At this point, the trochanter is removed from the needle. If the trochanter has some traces of blood, this confirms the fact that the needle is in the bone marrow cavity. The 60 cc syringe with 10 cc of heparin is attached to the bone marrow aspiration needle, and the plunger is pulled back 3 cc at a time, applying constant pressure. The flow of bone marrow will be seen flowing into the syringe. To maximize the number of cells obtained, after 5-7 cc of bone marrow is obtained it is recommended to turn the needle about 90° in one direction to obtain cells from different areas of the bone marrow cavity. 50 cc of bone marrow should be aspirated into the syringe. In addition to the 10 cc of heparin intravenously in the syringe, this will make up a total of 60 cc. The needle and the syringe are then withdrawn from the PSIS. Pressure should be applied to the site to prevent bleeding, and an appropriate bandage applied to the site.

The bone marrow aspirate should be filtered to remove any bone particles that may have been collected during the above procedure. The 60 cc syringe containing the bone marrow aspirate is attached to the previously heparinized 270 µm filter at the entrance point and another 60 cc syringe is attached to the exit point of the filter. The aspirate is pushed through the filter and collected into the empty syringe at the exit point of the filter.

The filtered aspirate is then transferred into a centrifuge tube and centrifuged for 2.5 minutes at 3800 RPM. This first centrifugation step separates the bone marrow aspirate into plasma on top, and bone marrow cells at the bottom of the tube. Preferably all of the plasma on the top of the cell layer is aspirated into a 60 cc syringe. Using another syringe (e.g., a 3 cc syringe) 2 ccs of the bone marrow cell layer are aspirated into the syringe. The 3 cc syringe containing the 2 cc cell layer is then attached to a second centrifugation tube, and the contents of the syringe is transferred into the tube. The 60 cc syringe containing the plasma collected from the first centrifuge is attached to the same tube, and the plasma is transferred into the second centrifugation tube. This solution is then centrifuged for 7 minutes at 3800 RPM. This step separates plasma from a buffy coat of bone marrow cells at the bottom of the tube. The excess plasma should be aspirated using the syringe, leaving only about 23 cc of plasma in the tube. The buffy coat is then re-suspended into the plasma by agitating the tube in a circular motion. The result is a bone marrow concentrate.

7 cc of PRP concentrate (prepared as previously described) is then added to the 23 cc of bone marrow concentrate. For the comfort of the patient, 5 cc of ropivacaine 0.2% is added to the bone marrow and PRP mixture. The final regenerative solution of bone marrow cells and PRP concentrate is then ready for injection into a patient using 5 cc syringes of solution for each injection site.

Figure 4B:
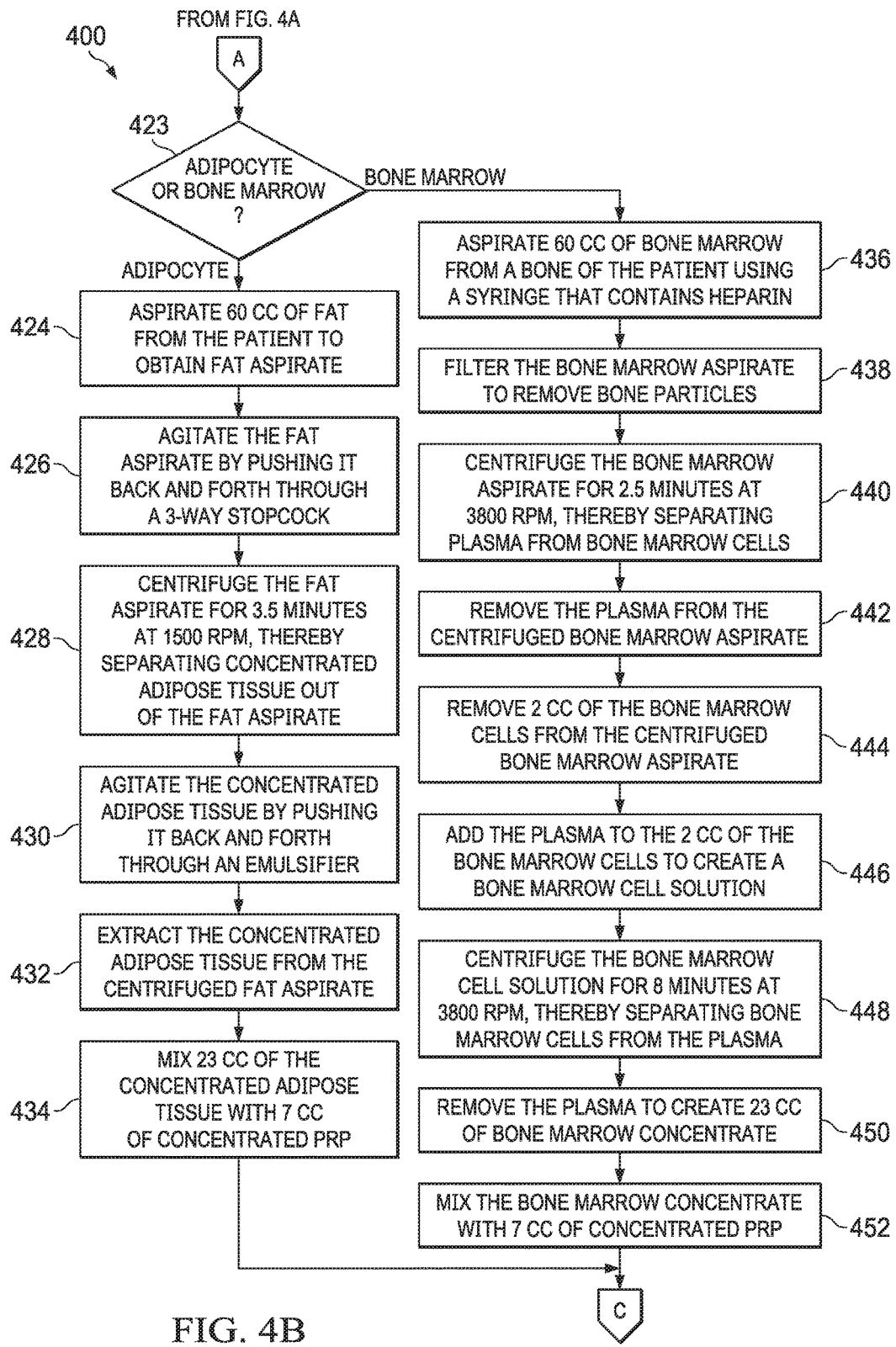
Figure 4C:
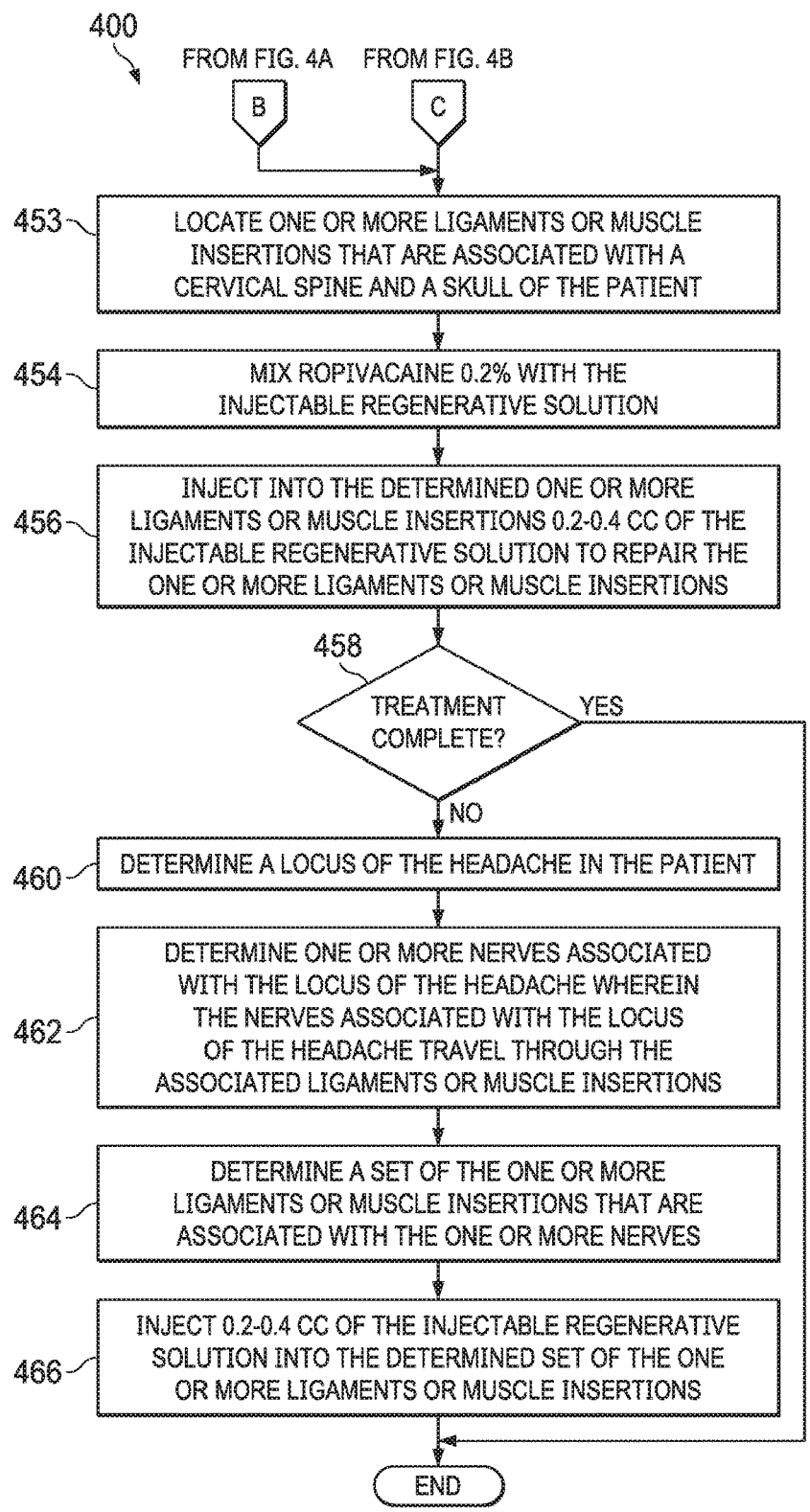

FIGS. 4A-4C illustrate a flow diagram of an example method 400 for treatment of migraines or other headaches according to embodiments of this disclosure. In this embodiment, the method 400 is performed by a doctor on a patient.

Referring now to FIG. 4A, beginning at block 404, when the doctor has determined that the patient is a candidate for regenerative injections to remedy migraines or other chronic headaches, the doctor determines whether an injectable regenerative solution will be PRP or stem cell based. As discussed above, this decision is discussed with the patient and may be cost dependent. Stem cell treatments are more effective, but more costly. PRP is prepared regardless of whether PRP or stem cell treatment is chosen, however, as PRP is used to activate the stem cells if stem cell injection is chosen. The PRP prepared for use with a stem cell injection is more concentrated, as described above.

At block 406, the doctor aspirates (or draws) 60 cc of venous blood from the patient using a syringe that contains 10 cc of sodium citrate as an anticoagulant. The doctor then, at block 408, centrifuges the blood for 1.6 minutes at 3800 RPM to separate plasma that includes a platelet suspension from red blood cells.

At block 410, the doctor removes the plasma and platelet suspension from the centrifuged blood. Then, at block 412, the doctor centrifuges the plasma and platelet suspension for 4 minutes at 3800 RPM to concentrate platelets within the plasma, thereby separating platelet rich plasma from platelet poor plasma.

At decision block 414, the doctor takes different courses of action based on whether a pure PRP injection is to be given to the patient (in which case blocks 416 and 418 are performed) or whether a stem cell injection with concentrated PRP is to be given to the patient (in which case blocks 420 and 422 are performed). The end result of this choice will be a PRP of different concentration.

If a pure PRP injection is to be given, then at block 416 the doctor removes the platelet poor plasma from the centrifuged plasma and platelet suspension obtained in block 412 until 10-15 mL of centrifuged plasma and platelet suspension remains. Then, at block 418, the doctor agitates the remaining 10-15 mL of centrifuged plasma and platelet suspension. The result is a pure PRP. The method 400 proceeds to block 454 below, where the PRP is prepared for injection and is injected into the patient.

If a stem cell injection is to be given, then at block 422 the doctor removes the platelet poor plasma from the centrifuged plasma and platelet suspension obtained in block 412 until 7 cc of plasma remains. Then, at block 422, the doctor agitates the remaining 7 cc of centrifuged plasma and platelet suspension. The result is a concentrated PRP that is ready to be mixed with a stem cell solution. The method 400 then proceeds to decision block 423 in FIG. 4B.

Referring now to FIG. 4B, at decision block 423 the doctor determines whether the stem cell injection will use adipocyte-derived stem cells or bone-marrow-derived stem cells, as discussed above. If the doctor will use adipocyte stem cells, the method proceeds to block 424. If the doctor will use bone marrow stem cells, the method proceeds to block 436.

If the doctor is using adipocyte stem cells, then at block 424, the doctor aspirates 60 cc of fat from the patient to obtain fat aspirate. The doctor then, at block 426, agitates the fat aspirate by pushing it back and forth through a 3-way stopcock. This breaks down any large portions of fat tissue in the fat aspirate.

At block 428, the doctor centrifuges the fat aspirate for 3.5 minutes at 1500 RPM, thereby separating concentrated adipose tissue out of the fat aspirate. At block 430, the doctor agitates the concentrated adipose tissue by pushing it back and forth through an emulsifier to further break down large portions of tissue in the concentrated adipose tissue.

At block 432, the doctor extracts the concentrated adipose tissue from the centrifuged fat aspirate, and at block 434 the doctor mixes 23 cc of the concentrated adipose tissue with 7 cc of concentrated PRP, as obtained at block 422. At this point, the adipocyte-based stem cell solution is ready to be prepared for injection, and the method proceeds to block 454 in FIG. 4C below.

Returning to the decision block 423, if the doctor is using bone marrow stem cells, then at block 436, the doctor aspirates 60 cc of bone marrow from a bone of the patient using a syringe that contains heparin as an anticoagulant. The doctor then, at block 438, filters the bone marrow aspirate to remove bone particles.

At block 440, the doctor centrifuges the bone marrow aspirate for 2.5 minutes at 3800 RPM, thereby separating plasma from bone marrow cells. At block 442, the doctor removes the plasma from the centrifuged bone marrow aspirate, and at block 444 the doctor removes 2 cc of the bone marrow cells from the centrifuged bone marrow aspirate.

At block 446, the doctor adds the plasma to the 2 cc of the bone marrow cells to create a bone marrow cell solution. Then the doctor, at block 448, centrifuges the bone marrow cell solution for 8 minutes at 3800 RPM, thereby separating bone marrow cells from the plasma. After centrifuging, at block 450, the doctor removes the plasma to create 23 cc of bone marrow concentrate, and at block 452 the doctor mixes the bone marrow concentrate with 7 cc of concentrated PRP, as obtained at block 422. At this point, the bone-marrow-based stem cell solution is ready to be prepared for injection, and the method proceeds to block 454 in FIG. 4C below.

Referring now to FIG. 4C, the doctor has prepared whichever regenerative injection solution was decided on with the patient. At block 453 the doctor locates one or more ligaments or muscle insertions that are associated with a cervical spine and a skull of the patient. In this embodiment, each of the sites marked with an "x" in FIGS. 1-3 is used as an injection site.

At block 454, the doctor mixes ropivacaine 0.2% with the injectable regenerative solution as an anesthetic. As noted above, ropivacaine is chosen because it is less toxic to platelets than other anesthetics.

At block 456, the doctor injects into the one or more ligaments or muscle insertions (located at block 453) 0.2-0.4 cc of the injectable regenerative solution to repair the one or more ligaments or muscle insertions. At this point an initial treatment is finished. The patient is allowed to recover and is monitored for progress.

At decision block 458, a check-up is performed on the patient to determine whether the patient has responded positively to the treatment, and if so, whether the patient needs further treatment. If the patient has substantially stopped having headaches, then no further treatment may be necessary (or the patient may decide to forego further treatment) and the method 400 ends. If the doctor determines that the patient is a candidate for further treatment, and the patient agrees to the treatment, then the method 400 proceeds to block 460.

At block 460, the doctor determines a locus of continuing headaches in the patient. As discussed above, this may be facilitated by the already-performed treatment, as the treatment will have regenerated some of the ligaments supporting the cervical spine of the patient, which may have reduced the severity migraine symptoms such that the patient is able to localize the pain.

At block 462, the doctor determines one or more nerves associated with the locus of the headache. At block 464, the doctor further determines which ligaments or muscle insertions the nerves travel through, allowing the doctor to determine which ligaments and muscles need further regenerative treatment to prevent irritation of the nerves.

At block 466, the doctor injects another 0.2-0.4 cc of the injectable regenerative solution into the newly determined set of the one or more ligaments or muscle insertions. This should result in repair of the ligaments and a reduction or elimination of nerve irritation in the patient, which in turn should reduce or eliminate migraine headache symptoms.

Although the present disclosure has been described with an exemplary embodiment, various changes and modifications may be suggested to one skilled in the art. It is intended that the present disclosure encompass such changes and modifications as fall within the scope of the appended claims.

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle.

What is claimed is:

1. A method for preventing and treating a headache in a patient, comprising:
    locating one or more ligaments or muscle insertions that are associated with a cervical spine and a skull of the patient; and
    injecting into the determined one or more ligaments or muscle insertions an injectable regenerative solution that includes platelet rich plasma (PRP) or stem cells to repair the one or more ligaments or muscle insertions.

2. The method of claim 1, further comprising:
    determining a locus of the headache in the patient;
    determining one or more nerves associated with the locus of the headache;
    determining a set of the one or more ligaments or muscle insertions that are associated with the one or more nerves; and
    injecting the injectable regenerative solution into the determined set of the one or more ligaments or muscle insertions.

3. The method of claim 2, wherein the nerves associated with the locus of the headache travel through the associated ligaments or muscle insertions.

4. The method of claim 1, further comprising preparing the injectable regenerative solution.

5. A method for preventing and treating a headache in a patient, comprising:
    locating one or more ligaments or muscle insertions that are associated with a cervical spine and a skull of the patient; and
    injecting into the determined one or more ligaments or muscle insertions an injectable regenerative solution that is derived from the patient to repair the one or more ligaments or muscle insertions;
    preparing the injectable regenerative solution;
    wherein the injectable regenerative solution is an adipocyte-based stem cell concentrate, and preparing the injectable regenerative solution comprises:
    aspirating fat from the patient to obtain fat aspirate;

centrifuging the fat aspirate, thereby separating concentrated adipose tissue out of the fat aspirate;
extracting the concentrated adipose tissue from the centrifuged fat aspirate; and
mixing the concentrated adipose tissue with concentrated platelet rich plasma (PRP).

6. The method of claim 5, further comprising:
prior to centrifuging, agitating the fat aspirate by pushing it back and forth through a 3-way stopcock; and
after centrifuging, agitating the concentrated adipose tissue by pushing it back and forth through an emulsifier.

7. The method of claim 5, further comprising:
aspirating 60 cc of fat;
centrifuging the fat aspirate for 3.5 minutes at 1500 RPM; and
mixing 23 cc of the concentrated adipose tissue with 7 cc of the concentrated PRP.

8. The method of claim 5, further comprising preparing the concentrated PRP by: aspirating venous blood from the patient;
centrifuging the blood to separate plasma that includes a platelet suspension from red blood cells;
removing the plasma and platelet suspension from the centrifuged blood;
centrifuging the plasma and platelet suspension to concentrate platelets within the plasma, thereby separating platelet rich plasma from platelet poor plasma; and
removing the platelet poor plasma from the centrifuged plasma and platelet suspension until 7 cc of plasma remains.

9. The method of claim 8, further comprises agitating the remaining 7 cc of centrifuged plasma and platelet suspension.

10. The method of claim 4, wherein the injectable regenerative solution is a platelet rich plasma (PRP), and preparing the injectable regenerative solution comprises:
aspirating venous blood from the patient;
centrifuging the blood to separate plasma that includes a platelet suspension from red blood cells;
removing the plasma and platelet suspension from the centrifuged blood;
centrifuging the plasma and platelet suspension to concentrate platelets within the plasma, thereby separating platelet rich plasma from platelet poor plasma; and
removing the platelet poor plasma from the centrifuged plasma and platelet suspension.

11. The method of claim 10, further comprising:
aspirating 60 cc of venous blood using a syringe containing 10 cc of sodium citrate anticoagulant;
centrifuging the blood for 1.6 minutes at 3800 RPM;
centrifuging the plasma and platelet suspension for 4 minutes at 3800 RPM;
removing the platelet poor plasma until 10-15 mL of centrifuged plasma and platelet suspension remains; and
agitating the remaining 10-15 mL of centrifuged plasma and platelet suspension.

12. The method of claim 4, wherein the injectable regenerative solution is a bone-marrow-based stem cell concentrate, and preparing the injectable regenerative solution comprises:
aspirating bone marrow from a bone of the patient to obtain bone marrow aspirate;
centrifuging the bone marrow aspirate, thereby separating plasma from bone marrow cells;
removing the plasma from the centrifuged bone marrow aspirate;
removing a portion of the bone marrow cells from the centrifuged bone marrow aspirate;
adding the plasma to the portion of the bone marrow cells to create a bone marrow cell solution;
centrifuging the bone marrow cell solution, thereby separating bone marrow cells from the plasma;
removing a portion of the plasma to create a bone marrow concentrate; and
mixing the bone marrow concentrate with concentrated platelet rich plasma (PRP).

13. The method of claim 12, further comprising, before centrifuging, filtering the bone marrow aspirate to remove bone particles.

14. The method of claim 12, further comprising:
aspirating 60 cc of bone marrow using a syringe that contains heparin anticoagulant;
centrifuging the bone marrow aspirate for 2.5 minutes at 3800 RPM;
removing 2 cc of the bone marrow cells from the centrifuged bone marrow aspirate;
centrifuging the bone marrow cell solution for 8 minutes at 3800 RPM;
removing the plasma until 23 cc of bone marrow concentrate remains;
agitating the 23 cc of bone marrow concentrate; and
mixing the 23 cc of bone marrow concentrate with 7 cc of the concentrated PRP.

15. The method of claim 12, further comprising preparing the concentrated PRP by:
aspirating venous blood from the patient;
centrifuging the blood to separate plasma and platelet suspension from red blood cells;
removing the plasma and platelet suspension from the centrifuged blood;
centrifuging the plasma and platelet suspension to concentrate platelets within the plasma, thereby separating platelet rich plasma from platelet poor plasma; and
removing the platelet poor plasma from the centrifuged plasma and platelet suspension until 7 cc of plasma remains.

16. The method of claim 15, further comprising agitating the remaining 7 cc of centrifuged plasma and platelet suspension.

17. The method of claim 1, further comprising:
mixing Ropivacaine 0.2% with the injectable regenerative solution before injecting the injectable regenerative solution.

18. The method of claim 1, wherein the one or more ligaments or muscle insertions comprise a majority of ligaments or muscle insertions in the cervical spine and skull of the patient.

19. The method of claim 1, wherein the one or more ligaments or muscle insertions are associated with at least one of superior or inferior occipital ridges, a mastoid process, a spinous process of vertebrae C2 to C7, laminae and facet joints of vertebrae C2 to C7, a transverse process of vertebrae C1 to C5, or first and second ribs.

20. The method of claim 1, wherein 0.2-0.4 cc of the injectable regenerative solution is injected.

* * * * *